United States Patent
Anwar et al.

(10) Patent No.: US 10,178,969 B2
(45) Date of Patent: Jan. 15, 2019

(54) STRESS DETECTION METHOD AND APPARATUS

(71) Applicant: Intel Corporation, Santa Clara, CA (US)

(72) Inventors: Naghma Anwar, San Jose, CA (US); Indira Negi, San Jose, CA (US); Vivek K. Menon, Overland Park, KS (US); Michael R. Rosen, Santa Clara, CA (US); Donald L. Gross, Hillsboro, OR (US); Ling Wang, San Jose, CA (US); Shea M. Dillon, Hillsboro, OR (US); Stephen C. Fenwick, Ashland, OR (US); Tom L. Simmons, Newbury Park, CA (US); Robert M. Negron, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 134 days.

(21) Appl. No.: 15/269,812

(22) Filed: Sep. 19, 2016

(65) Prior Publication Data
US 2018/0078187 A1 Mar. 22, 2018

(51) Int. Cl.
*A61B 5/02* (2006.01)
*A61B 5/16* (2006.01)
(Continued)

(52) U.S. Cl.
CPC .......... *A61B 5/165* (2013.01); *A61B 5/02416* (2013.01); *A61B 5/02438* (2013.01);
(Continued)

(58) Field of Classification Search
CPC ....... A61B 5/165; A61B 5/0476; A61B 5/742; A61B 5/486; A61B 5/746; A61B 5/7475;
(Continued)

(56) References Cited

U.S. PATENT DOCUMENTS 4,354,505 A 10/1982 Shiga
8,755,879 B2 6/2014 Hang et al.
(Continued)

OTHER PUBLICATIONS

Metz, R., "Google Glass Can Now Track Your Stress Level," https://www.technologyreview.com/s/530521/google-glass-can-now-track-your-stress-level/, last visited Sep. 8, 2016, 5 pages.
(Continued)

*Primary Examiner* — Rex R Holmes
(74) *Attorney, Agent, or Firm* — Schwabe, Williamson & Wyatt, P.C.

(57) ABSTRACT

Embodiments of the present disclosure provide techniques and configurations for an apparatus for stress event detection. In some embodiments, the apparatus may be a wearable device and may include at least one first sensor disposed on the wearable apparatus to generate a first sensor signal indicative of a brain activity of a user, at least one second sensor disposed on the wearable apparatus to generate a second sensor signal indicative of a heart rate of the user, and at least one third sensor disposed on the wearable apparatus to generate a third sensor signal indicative of a respiration rate of the user. The apparatus may further include a controller coupled with the at least first, second, and third sensors, to detect a stress event for the user, based at least in part on the first, second, and third sensor signals. Other embodiments may be described and/or claimed.

9 Claims, 7 Drawing Sheets

(51) Int. Cl.
*A61B 5/00* (2006.01)
*A61B 5/024* (2006.01)
*A61B 5/08* (2006.01)
*A61B 5/0476* (2006.01)

(52) U.S. Cl.
CPC .......... *A61B 5/0476* (2013.01); *A61B 5/0816* (2013.01); *A61B 5/4064* (2013.01); *A61B 5/486* (2013.01); *A61B 5/6803* (2013.01); *A61B 5/7282* (2013.01); *A61B 5/746* (2013.01); *A61B 2560/0223* (2013.01); *A61B 2562/028* (2013.01)

(58) Field of Classification Search
CPC . A61B 5/02416; A61B 5/6803; A61B 5/7282; A61B 5/0816; A61B 5/02438; A61B 5/4064; A61B 2560/0223; A61B 2562/028

See application file for complete search history.

(56) References Cited

U.S. PATENT DOCUMENTS

| | | |
|---|---|---|
| 8,860,867 B2 | 10/2014 | Sako et al. |
| 9,144,405 B2 | 9/2015 | Kim et al. |
| 9,285,589 B2 | 3/2016 | Osterhout et al. |
| 2007/0249952 A1 | 10/2007 | Rubin et al. |
| 2012/0029322 A1 | 2/2012 | Wartena et al. |
| 2013/0060097 A1 | 3/2013 | Rubin |
| 2014/0275829 A1 | 9/2014 | Berezhnyy et al. |
| 2015/0351655 A1* | 12/2015 | Coleman .............. A61B 5/0482 600/301 |
| 2016/0077547 A1 | 3/2016 | Aimone et al. |
| 2017/0367651 A1* | 12/2017 | Tzvieli ................. A61B 5/0077 |
| 2018/0078164 A1 | 3/2018 | Menon et al. |

OTHER PUBLICATIONS

Zheng, Y., et al., "Unobtrusive and Multimodal Wearable Sensing to Quantify Anxiety," IEEE Sensors Journal, vol. 16, No. 10, May 15, 2016, pp. 3689-3696.

Zheng, Y., et al., "Unobtrusive Sensing and Wearable Devices for Health Informatics," IEEE Transactions on Biomedical Engineering, vol. 61, No. 5, May 2014, pp. 1538-1554.

Office Action dated Jun. 21, 2018 for U.S. Appl. No. 15/269,615, 47 pages.

* cited by examiner

STRESS DETECTION METHOD AND APPARATUS

FIELD

Embodiments of the present disclosure generally relate to the fields of wearable devices, and more particularly, to wearable devices also configured to detect stress based on readings provided by sensors disposed on the wearable devices.

BACKGROUND

Stress is one of prevalent maladies in today's world. It afflicts people of all ages and cultures and affects a person's ability to concentrate and work efficiently. An important part of stress relief is stress detection. Current medical procedures of stress detection involve taking saliva or blood samples. These procedures may not always be user-friendly because people normally do not have time or interest to measure their stress level.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example and not by way of limitation in the figures of the accompanying drawings.

DETAILED DESCRIPTION

Embodiments of the present disclosure include techniques and configurations for an apparatus and method for stress event detection. In some embodiments, the apparatus may be a wearable device and may include at least one first sensor disposed on the wearable apparatus to generate a first sensor signal indicative of a brain activity of a user, at least one second sensor disposed on the wearable apparatus to generate a second sensor signal indicative of a heart rate of the user, and at least one third sensor disposed on the wearable apparatus to generate a third sensor signal indicative of a respiration rate of the user. The apparatus may further include a controller coupled with the at least first, second, and third sensors, to detect a stress event for the user, based at least in part on the first, second, and third sensor signals.

In some embodiments, the apparatus may comprise a head-fitting device to be mounted at least partly around the user's head, such as eyeglasses. The first sensor may be disposed on the head-fitting device to provide direct contact with or proximity to a user's head, in response to application of the head-fitting device to the user's head. In embodiments, the first sensor may comprise capacitive electrodes, to sense electroencephalogram (EEG) indicative of the brain activity of the user.

The second sensor may be disposed on the head-fitting device to provide direct contact with the user's head, in response to application of the head-fitting device to the user's head. In embodiments, the second sensor may comprise an optical hear rate sensor, to sense a photoplethysmogram (PPG) indicative of the heart rate of the user.

The third sensor may be disposed on the head-fitting device to provide direct contact with or proximity to the user's head, in response to application of the head-fitting device to the user's head. In embodiments, the third sensor may comprise a piezoelectric sensor, to sense vibrations in the user's head produced by user's respiration; or a digital or analog microphone, to sense audio signals indicative of the user's respiration rate.

In the following detailed description, reference is made to the accompanying drawings that form a part hereof, wherein like numerals designate like parts throughout, and in which are shown by way of illustration embodiments in which the subject matter of the present disclosure may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

For the purposes of the present disclosure, the phrase "A and/or B" means (A), (B), (A) or (B), or (A and B). For the purposes of the present disclosure, the phrase "A, B, and/or C" means (A), (B), (C), (A and B), (A and C), (B and C), or (A, B, and C).

The description may use perspective-based descriptions such as top/bottom, in/out, over/under, and the like. Such descriptions are merely used to facilitate the discussion and are not intended to restrict the application of embodiments described herein to any particular orientation.

The description may use the phrases "in an embodiment" or "in embodiments," which may each refer to one or more of the same or different embodiments. Furthermore, the terms "comprising," "including," "having," and the like, as used with respect to embodiments of the present disclosure, are synonymous.

The term "coupled with," along with its derivatives, may be used herein. "Coupled" may mean one or more of the following. "Coupled" may mean that two or more elements are in direct physical, electrical, or optical contact. However, "coupled" may also mean that two or more elements indirectly contact each other, but yet still cooperate or interact with each other, and may mean that one or more other elements are coupled or connected between the elements that are said to be coupled with each other. The term "directly coupled" may mean that two or more elements are in direct contact.

Figure 1:
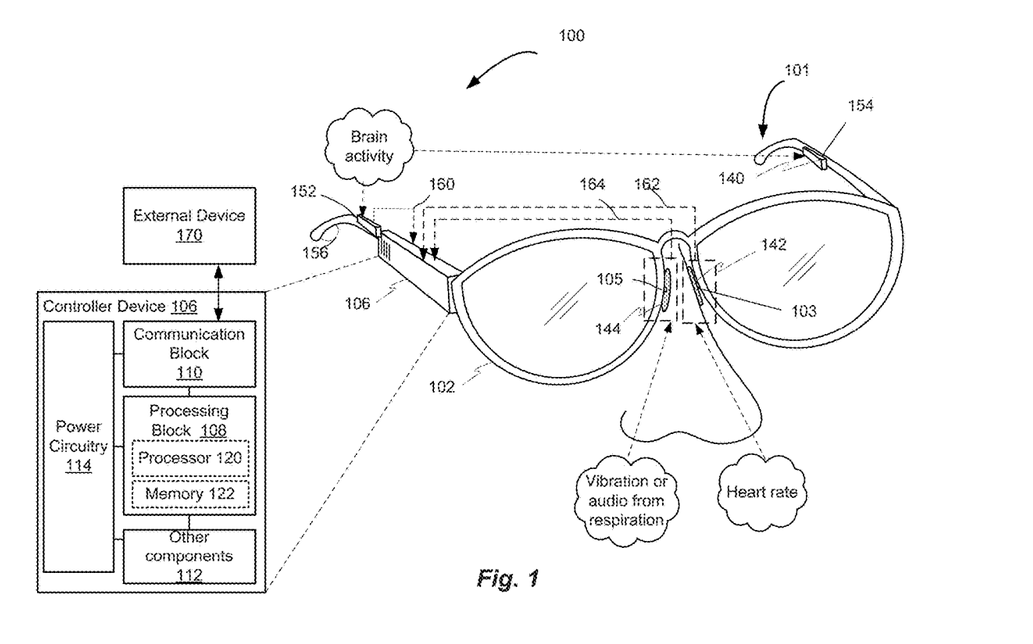
FIG. 1 is a diagram illustrating an example wearable apparatus for stress event detection, in accordance with some embodiments.

FIG. 1 is a diagram illustrating an example wearable apparatus for stress event detection, in accordance with some embodiments. The apparatus 100 may comprise a wearable device, to be worn on or around a user's head. A plurality of sensors may be disposed around the apparatus 100 to provide readings of the user's physiological context, such as the user's brain activity, heart rate, and respiration rate. The apparatus may further include a controller 106 coupled with the sensors, to receive the readings provided by the sensors, and detect a stress event for the user, based at least in part on sensors' readings. In embodiments, the apparatus may be configured to have controller 106 continuously receive the readings provided by the sensors.

Example implementations of the apparatus 100 may include eyeglasses, helmets, headsets, diadems, caps, hats, or other types of headwear. While examples of specific implementations (e.g., in eyeglasses) and/or technologies (e.g., optical, capacitive, audio, or piezoelectric sensors, wireless communications, etc.) may be employed herein, these examples are presented merely to provide a readily comprehensible perspective from which the more generalized devices, methods, etc. described herein may be understood.

As noted above, the apparatus 100 may comprise a wearable device, such as eyeglasses 101, in the example illustrated in FIG. 1. The apparatus 100 may include a frame 102 of eyeglasses 101. The frame 102 is described herein as a part of the apparatus 100 (in this example, eyeglasses 101) for the sake of explanation. Other applications or configurations of an apparatus 100 may result in implementations that remain consistent with the teachings presented herein.

The plurality of sensors 140, 142, 144 may be disposed on the apparatus 100, such as on the frame 102, including nose pads 103, 105 and/or frame sides, as shown in FIG. 1. The sensors 140, 142, 144 may be mounted on the frame 102 via mechanical attachment (e.g., screw, nail or other fastener), adhesive attachment (e.g., a glue, epoxy, etc.) or may be incorporated within the structure of the frame 102 or nose pads 103, 105.

One of the effects of a stress event may be increased brain activity of a user. Accordingly, it may be beneficial to capture brain waves to detect a heightened brain activity of the user during a stressful situation. One or more of the plurality of sensors of the apparatus 100, e.g., the sensor 140 may be configured to sense brain activity, such as detect hemispheric asymmetry in brain waves.

In embodiments, the sensor 140 may comprise, for example, an EEG sensor, such as, for example, a capacitive sensor having two EEG electrodes 152, 154 embedded in the frame 102. As shown, the right and left EEG sensor electrodes 152, 154 may be embedded into the left and right sides of the frame 102, respectively. The EEG electrodes 152, 154 may be capacitive electrodes and may not require application of any type of conductive gel on the skin.

The example placement of the EEG electrodes 152, 154 on the apparatus 100 is shown for purposes of illustration. In general, the EEG electrodes 152, 154 may be placed anywhere on the apparatus 100 (e.g., anywhere on the frame 102) to provide proximity to or direct contact with the user's head, in order to provide brain wave readings in a form of electronic signal of a desired strength. Another capacitive EEG electrode to provide a reference capacitance may be placed anywhere on the frame 102. For example, the reference EEG electrode 156 may be placed on the side of the frame 102 corresponding to the edge of the user's temple behind the ear, as shown.

Change in heart rate and change in heart rate variability may also indicate the effect of mental stress. These symptoms may be captured using the sensor 142, which may sense a heart rate of the user. The sensor 142 may comprise a PPG sensor, such as, for example, an optical heart rate sensor. The sensor 142 may be placed in any part of the apparatus 100 (e.g., frame 102), to provide direct contact with the user's head, in response to application of the apparatus 100 to the user's head, in order to provide PPG readings in a form of an electronic signal. For example, the sensor 142 may be placed on the nose pad 103, as shown. In general, the sensor 142 may be disposed to provide direct contact with the user's head, such as around the temple of the user's head, ears, forehead, or the like.

Mental stress may also manifest itself in a change (e.g., increase) of a breathing rate of the user. For example, long and deep breathing may be associated with a relaxed state of mind, while short and shallow breathing may indicate a stressful state of mind. To capture this effect, the sensor 144 of the apparatus 100 may be configured to sense user's perspiration. The sensor 144 may comprise, for example, a digital or analog microphone to sense audio signals indicative of the user's respiration rate, and convert the sensed signals into an electronic signal.

In another example, the sensor 144 may comprise a piezoelectric sensor such as a diaphragm or other piezoelectric transducer, to sense vibration (e.g., mechanical pressure waves) occurring in portions of the user's head (e.g., nasal bones) and produced by user's respiration, and convert the sensed vibration into an electronic signal. In some embodiments, the sensor 144 may comprise any type of sensors responsive to vibration, such as, for example, microelectromechanical systems (MEMS) accelerometer or the like.

The sensor 144 may be disposed in any part of the apparatus 100 (e.g., frame 102), to provide direct contact with or at least proximity to the user's head, in response to application of the apparatus 100 to the user's head. For example, the sensor 144 may be placed on the nose pad 105, as shown, to be in contact with, or at least proximate to, the nose of a user wearing the apparatus 100. In general, the sensor 144 may be disposed to provide direct contact with or proximity to the user's nose, temple of the user's head, ears, forehead, or the like.

The apparatus 100 may further include a controller device 106, which in some embodiments may also be disposed on the apparatus 100 (e.g., the frame 102) as shown. The controller device 106 may be electrically and/or communicatively coupled with the sensors 140, 142, 144, to receive and process sensor signals 160, 162, 164 provided by the sensors 140, 142, 144 respectively and to detect a stress event for the user, based at least in part on a result of processing the signals 160, 162, and 164.

The controller device 106 may comprise, for example, a processing block 108, to process the signal 160, 162, 164, and communication block 110 to transmit a result of the processing to an external device 170 (e.g., to an application residing on a smartphone) for further processing, such as to identify and record a stress event for the user, or to alert the user of the stress event and provide recommendations as to how to mitigate the stress effect.

The processing block 108 may comprise at least a processor 120 and memory 122. The processing block 108 may include components configured to record and process the readings of the signals 160, 162, 164. The processing block 108 may provide these components through, for example, a plurality of machine-readable instructions stored in the memory 122 and executable on the processor 120. The controller device 106 may record the signals 160, 162, 164 and store (e.g., buffer) the recorded readings, for example, in the memory 122, for further analysis and processing, e.g., in real time or near-real time.

The processor 120 may include, for example, one or more processors situated in separate components, or alternatively one or more processing cores embodied in a component (e.g., in a System-on-a-Chip (SoC) configuration), and any processor-related support circuitry (e.g., bridging interfaces, etc.). Example processors may include, but are not limited to, various microprocessors including those in the Pentium®, Xeon®, Itanium®, Celeron®, Atom®, Quark®, Core® product families, or the like.

Examples of support circuitry may include host side or input/output (I/O) side chipsets (also known as northbridge and southbridge chipsets/components) to provide an interface through which the processor 120 may interact with other system components that may be operating at different speeds, on different buses, etc. in the controller device 106. Some or all of the functionality commonly associated with the support circuitry may also be included in the same physical package as the processor.

The memory 122 may comprise random access memory (RAM) or read-only memory (ROM) in a fixed or removable format. RAM may include volatile memory configured to hold information during the operation of device 106 such as, for example, static RAM (SRAM) or Dynamic RAM (DRAM). ROM may include non-volatile (NV) memory circuitry configured based on basic input/output system (BIOS), Unified Extensible Firmware Interface (UEFI), etc. to provide instructions when the controller device 106 is activated, programmable memories such as electronic programmable ROMs (erasable programmable read-only memory), Flash, etc. Other fixed/removable memory may include, but is not limited to, electronic memories such as solid state flash memory, removable memory cards or sticks, etc.

The communication block 110 may be communicatively coupled with the external device 170 and may include one or more radios capable of transmitting and receiving signals using various suitable wireless communications techniques. Such techniques may involve communications across one or more wireless networks. Some example wireless networks include (but are not limited to) wireless local area networks (WLANs), wireless personal area networks (WPANs), wireless metropolitan area network (WMANs), cellular networks, and satellite networks. In communicating across such networks, the communication block 110 may operate in accordance with one or more applicable standards in any version. To this end, the communication block 110 may include, for instance, hardware, circuits, software, or any combination thereof that allows communication with external computer systems.

In some specific non-limiting examples, the communication block 110 may comport with the Institute of Electrical and Electronics Engineers (IEEE) 802.11 standard (e.g., Wi-Fi), a Bluetooth®, ZigBee®, near-field communication, or any other suitable wireless communication standard. In addition, the communication block 110 may comport with cellular standards such as 3G (e.g., Evolution-Data Optimized (EV-DO), Wideband Code Division Multiple Access (W-CDMA)) and/or 4G wireless standards (e.g., High Speed Packet Access (HSPA), Worldwide Interoperability for Microwave Access (WIMAX), Long-Term Evolution (LTE)).

Still referring to FIG. 1, the apparatus 100 may further include a power circuitry block 114 configured to provide power supply to the components of the controller device 106. In some embodiments, the power circuitry block 114 may be configured to power on the controller device 106 continuously or periodically, in order to save battery power. In some embodiments, the power circuitry block 114 may be configured to power on the controller device 106 on a "wake-up" basis, e.g., in response to sensor signal provision by the sensors 140, 142, 144. The power circuitry block 114 may include internal power sources (e.g., battery, fuel cell, etc.) and/or external power sources (e.g., power grid, electromechanical or solar generator, external fuel cell, etc.) and related circuitry configured to supply device 106 with the power needed to operate.

The controller device 106 may include other components 112 that may be necessary for functioning of the apparatus 100. Other components 112 may include, for example, hardware and/or software to allow users to interact with the controller device 106 such as, for example, various input mechanisms (e.g., microphones, switches, buttons, knobs, keyboards, speakers, touch-sensitive surfaces, one or more sensors configured to capture images and/or sense proximity, distance, motion, gestures, orientation, biometric data, etc.) and various output mechanisms (e.g., speakers, displays, lighted/flashing indicators, electromechanical components for vibration, motion, etc.). The hardware in other components 112 may be incorporated within the controller device 106 and/or may be external to the device 106 and coupled to device 106 via a wired or wireless communication medium.

Figure 2:
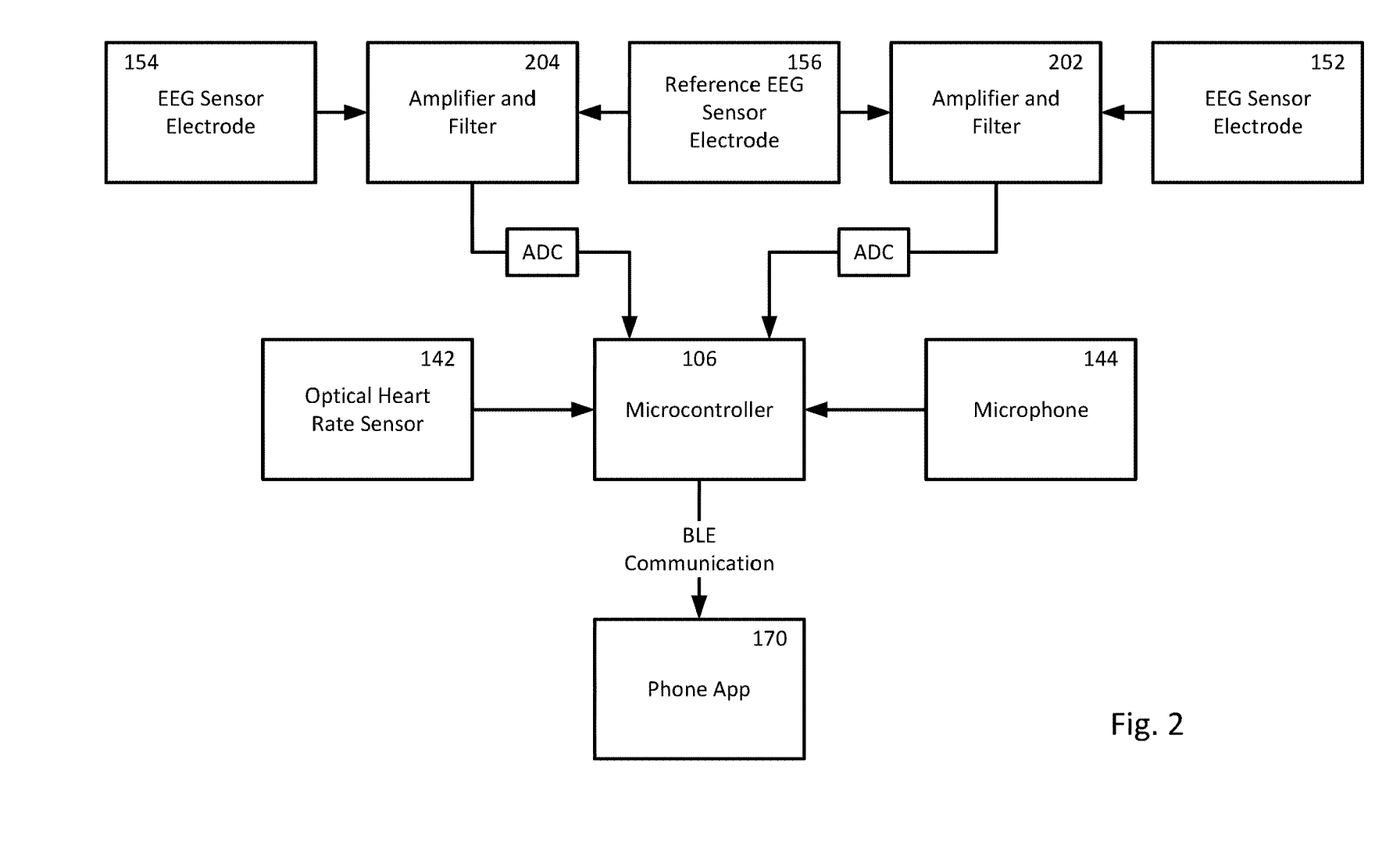
FIG. 2 is an example block diagram of some components of the apparatus of FIG. 1, in accordance with some embodiments.

FIG. 2 is an example block diagram of some components of the apparatus of FIG. 1, in accordance with some embodiments. For ease of understanding, like elements of FIG. 1 and subsequent figures are indicated by like numerals.

As shown, the outputs from the EEG electrodes 152, 154 (right and left in the case of the eyeglass embodiment), and from the reference EEG electrode 156 may be fed into instrumentation amplifiers and filters 202, 204 to capture the desired brain frequencies. This data may be provided to the controller device 106 (e.g., through an analog to digital converter (ADC), as shown) for further processing.

Similarly, the signals from the sensors 142 and 144 may be provided to the controller device 106, as shown. The controller device 106 may process the sensor signals, and provide the processed data to the external device 170 (e.g., smartphone application) for further processing, via a communication channel, e.g., Bluetooth® Low Energy (BLE).

Figure 3:
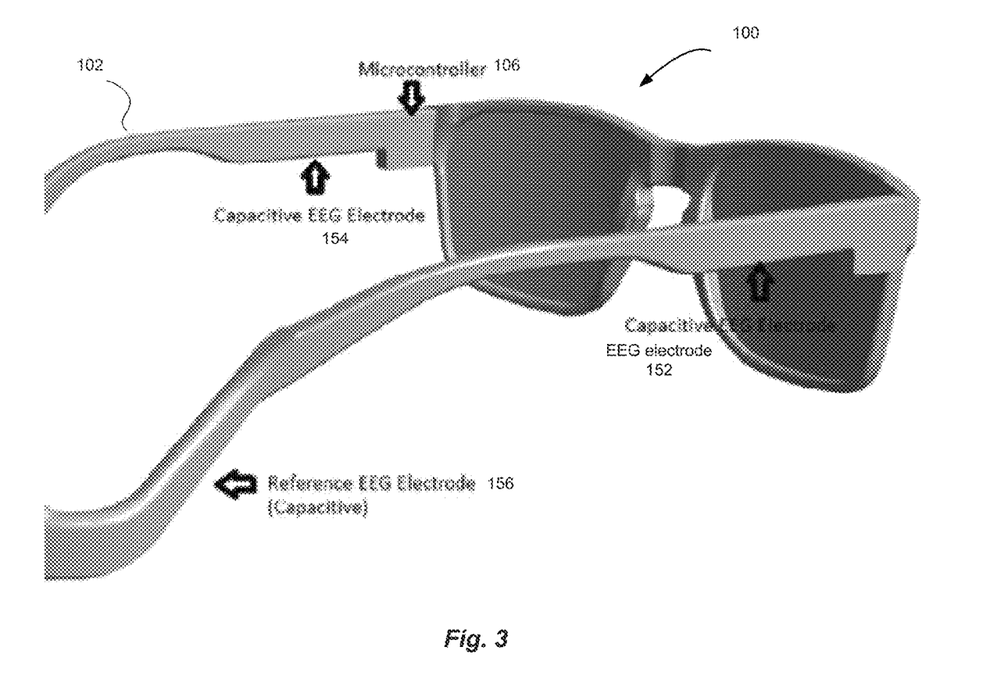
FIGS. 3-5 illustrate an example configuration of the apparatus of FIG. 1, in accordance with some embodiments.
Figures 4, 5:
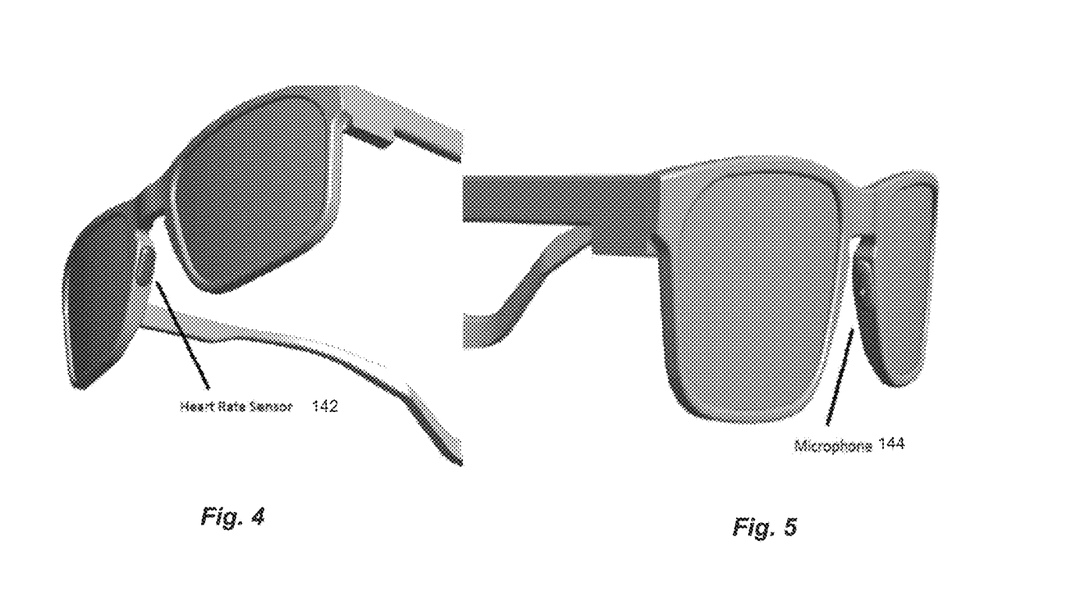

FIGS. 3-5 illustrate an example configuration of the apparatus of FIG. 1, in accordance with some embodiments. As shown in FIG. 3, the EEG electrodes 152, 154 may be embedded into the frame 102 (on different sides) for increased/maximum skin contact or at least proximity to the user's head. The reference EEG electrode 156 may be placed closer to the back of the side of the frame 102, as shown.

The controller device 106 (e.g., microcontroller) may be placed inside a cavity in the frame 102. The controller device 106 may be included in a flexible printed circuit board (PCB) that may be disposed around the glass frame 102. The amplifiers and filters 202, 204 for the electrodes may also be a part of the flexible PCB. The electrodes 152, 154, 156, which are disposed on the frame 102, may be connected to these amplifiers, e.g., using solder pads. The controller device 106 may execute a routine to measure the brain activity of the user, as described below.

As shown in FIG. 4, the heart rate sensor 142 may be embedded into one of the nose pads, for increased/maximum skin contact. This sensor may be configured to continuously monitor the heart rate of the user. The data from the sensor 142 may be fed to the controller device 106, e.g., using Inter-Integrated Circuit (I2C) protocol. The controller device 106 may execute a routine to measure the heart of the user, as described below.

As shown in FIG. 5, the sensor 144 (e.g., a microphone) may be placed inside one of the nose pads of the frame 102. This microphone may continuously capture the breathing sound of the user. The audio data may be provided to the controller device 106 using Inter-Integrated Circuit Sound (I2S) protocol. The controller device 106 may run a routine to determine the respiration rate.

Figure 6:
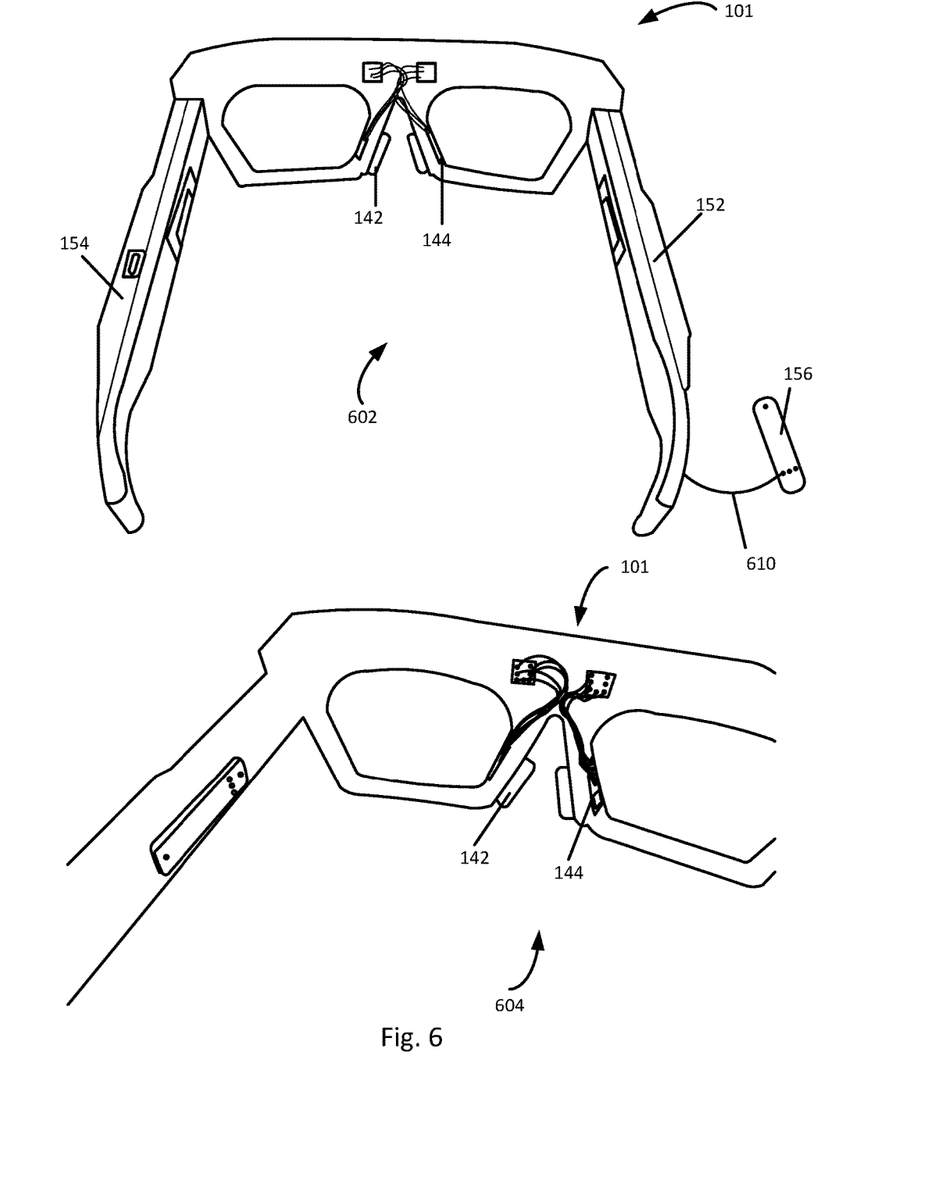
FIGS. 6-7 illustrate various views of the example apparatus of FIG. 1 implemented in an eyeglasses form factor, in accordance with some embodiments.
Figure 7:
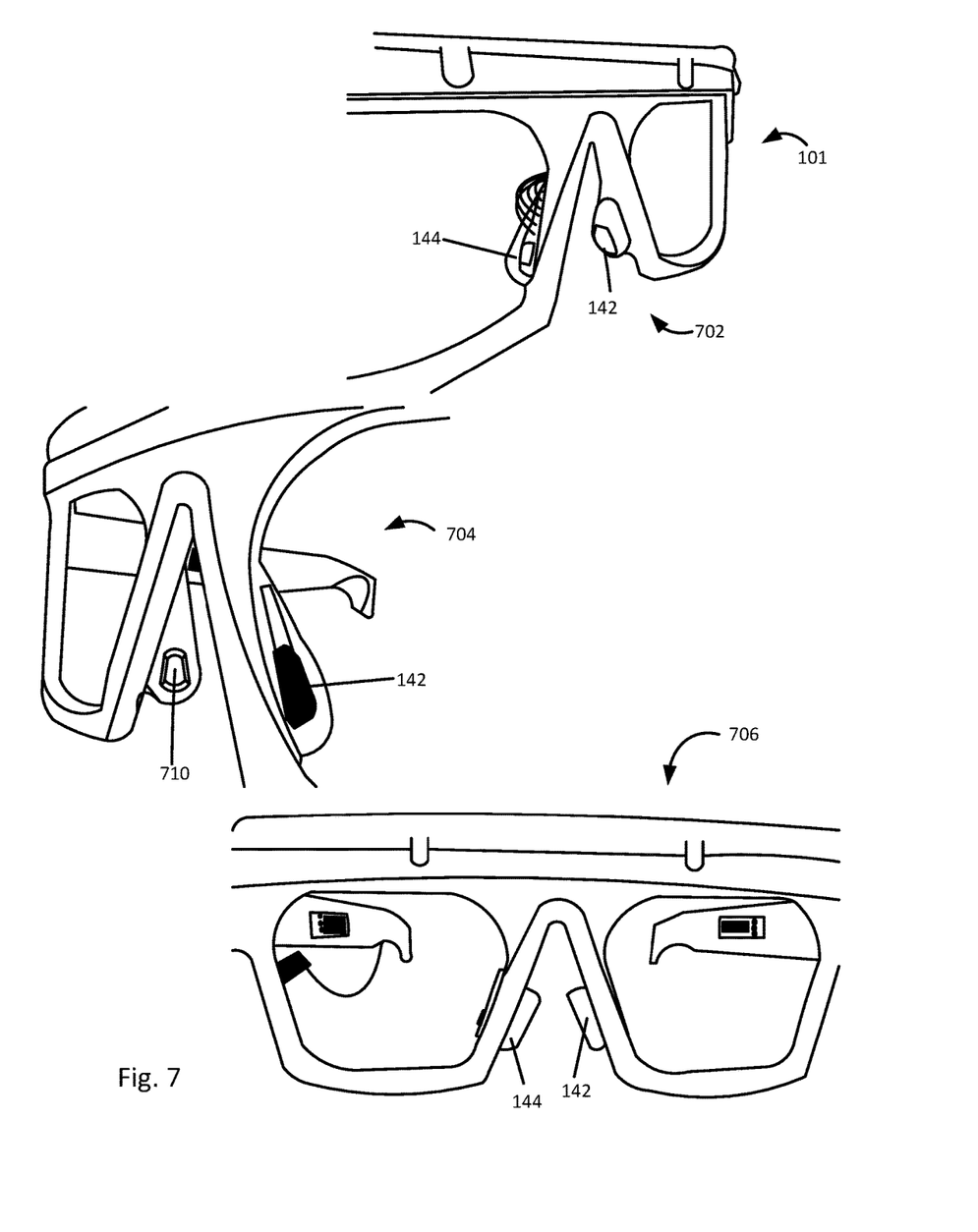

FIGS. 6-7 illustrate various views of an example apparatus of FIG. 1 implemented in an eyeglasses form factor, in accordance with some embodiments. As shown in views 602 and 604 of FIG. 6, and views 702, 704, and 706 of FIG. 7, the heart rate sensor 142 is attached to the left nose pad, and the microphone 144 is attached to the right nose pad of the eyeglasses 101. An entry hole 710 in view 704 indicates the place for the sound waves to enter the sensor 144. As shown in view 602, the EEG electrodes 152, 154 are removably attached to the respective sides of the frame of the glasses 101. The EEG reference electrode 156 is attached to the glasses 101 with a wire 610, to be disposed behind the ear of the user when the user puts on eyeglasses 101. In embodiments, the EEG electrodes may be supported by a separate PCB if the electrodes may be too brittle to be supported by the flexible PCB inside the glasses. Thus, the the electrodes may be fabricated on a separate PCB which may be connected to the main PCB, e.g., using wires.

As described above, the controller device 106 may be getting data signals from three different sources: optical heart rate sensor, a sensor to measure respiration (e.g., microphone) and an EEG sensor. The controller device 106 may run, substantially in parallel, three different routines to detect and identify changes in heart rate and heart rate variability, respiration rate, and brain waves from both brain hemispheres. Threshold values may be set for each of the respective signal types. When the signal values for each respective type of measurement (e.g., heart rate, respiration rate, and brain wave) exceed their respective threshold levels (e.g., within a same time period, such as sensor polling period), a stress event may be detected.

As described in reference to FIG. 1, the controller device 106 may have communication capabilities, implemented as the communication block 110. In some embodiments, the communication block 110 may comprise an inbuilt BLE chip. Whenever a stress event is detected, the controller device 106 may send a notification to a smart phone application (e.g., residing on an external device 170). The smart phone application may alert the user about the stress event. The application may, for example, prompt the user to take a deep breath to relieve stress, stop working, sit or lie down, stop moving, or the like. The smart phone application may be also used to display the various outputs of sensors in real time. For example, the smartphone application may show the heart rate, respiration rate and hemispheric asymmetry of the user in real or near-real time using charts and graphs.

Figure 8:
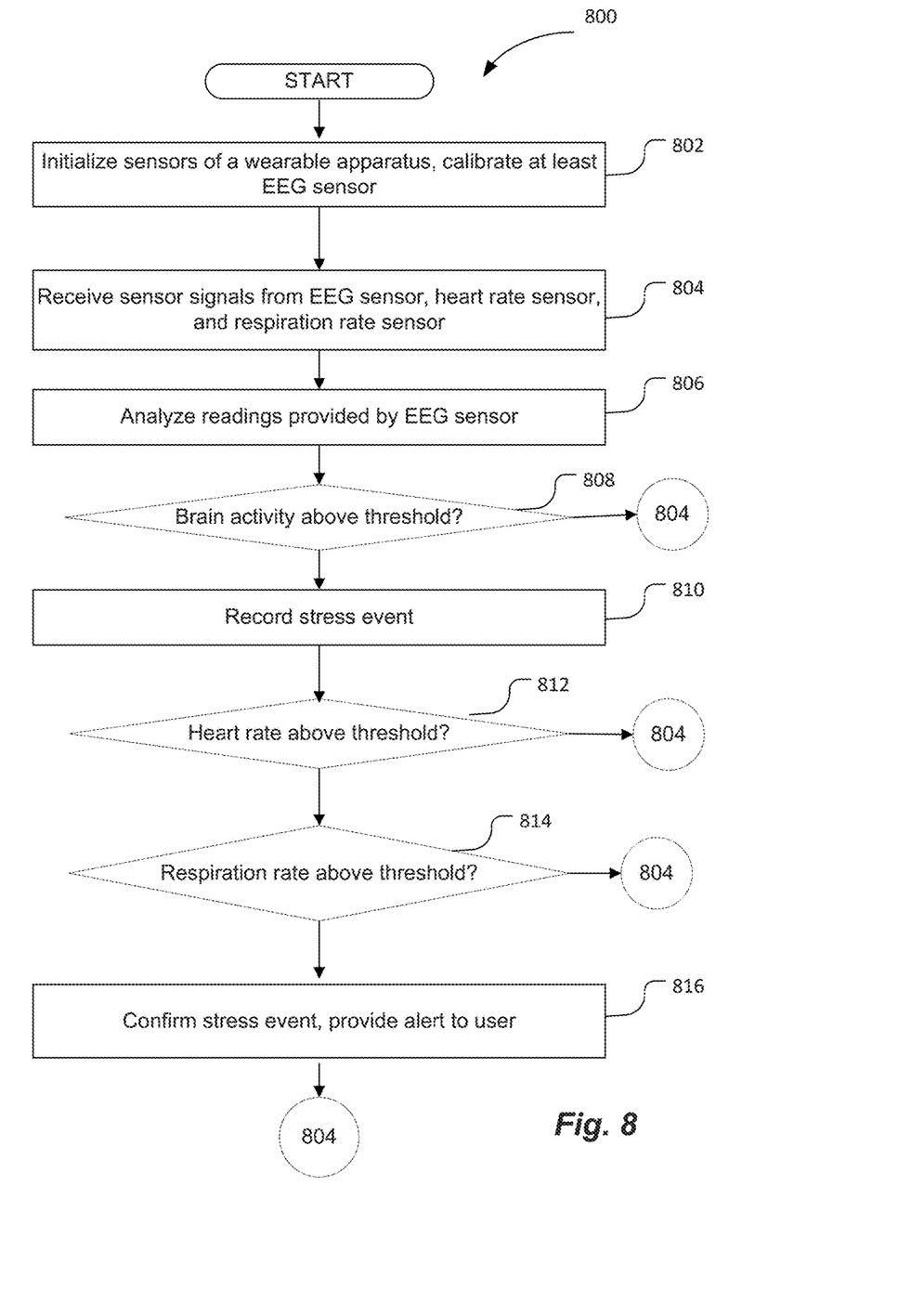
FIG. 8 is an example process flow diagram for detecting a stress event with a wearable apparatus, in accordance with some embodiments.

FIG. 8 is an example process flow diagram for detecting a stress event with a wearable apparatus, in accordance with some embodiments. The process 800 may comport with some of the apparatus embodiments described in reference to FIGS. 1-7. For example, the apparatus may comprise the wearable apparatus 100 of FIG. 1 and the process 800 may be performed by the controller 106 of the apparatus 100. In alternate embodiments, the process 800 may be practiced with more or fewer operations, or a different order of the operations.

The process 800 may begin at block 802 and include initializing sensors of a wearable apparatus, during which at least a brain activity detection (e.g., EEG) sensor may be calibrated. The initialization task may run only once, to set data values for the sensors to start sensing respective readings, such as brain activity, heart rate, and respiration rate. The example initialization routine for embodiments with ADC coupled to electrode sensors 152 and 154, may be provided as follows:

1. Run a loop at a sampling rate (e.g., 10 second loop at 200 Hz) to pull data from pins 0 and 1 of the ADC with which the EEG sensor is connected, and storing the pulled data into respective data arrays, array0 and array1. The pin numbers are the ADC out pins. Since there are two EEG electrodes on each side of the glasses, two ADC outputs, one from each electrode, may be used. The data collected from the two electrodes may be kept in separate arrays in order to perform the Fast Fourier Transform (FFT). In other words, the dominant frequency may be identified in each array by performing FFT on each array. Then, the highest amplitude of these FFTs may be determined. A ratio of these two dominant frequency's highest amplitudes may be determined, which may indicate hemispheric asymmetry of the brain waves.
2. Perform Fast Fourier Transform on array0 and array1 to generate transformed data arrays FFT0 and FFT1. The Fourier Transform may be a representation of the frequency components (spectrum) of the signals in the frequency domain, as opposed to the temporal domain. In FFT, the more prominent frequency may be detected on the signal spectrum. Capturing brain waves may include capturing alpha and beta waves, which fall between 8 to 40 Hz. Accordingly, data that falls beyond that range (e.g., above 40 Hz) may be disregarded.
3. Find maximum value of FFT0 and FFT1 between 3 Hz and 17 Hz on both arrays. Alpha waves and lower beta waves, which fall between 3 and 17 Hz, may be of interest for brain activity identification purposes.
4. Divide the peak amplitude value of FFT1 by the peak amplitude value of FFT0 to determine left to right alpha asymmetry index, to identify brain activity asymmetry as related to brain hemispheres. 5. Repeat operations 1-4 a number of (e.g., three) times to get several (e.g., three) values for alpha index and for beta index, then take the average and calculate alpha and beta asymmetry index baselines. Asymmetry alpha and beta index baselines may be global variables. In general, every individual may have his or her own baseline asymmetry across the brain hemisphere. Accordingly, the EEG sensor output may be calibrated for a particular individual, by taking several (three) alpha ratios and beta ratios from the two EEG electrodes and then taking average of both.

While the initialization task described above may be run once, the actions of a routine that begins at block 804 may run periodically after every specified interval. Accordingly, at block 804, once the initialization is complete, the process 800 may include begin receiving readings from the brain activity detection sensor, heart rate sensor, and respiration rate sensor of the apparatus. The sensors may sample data continuously and store the data in the flash memory (e.g., memory 122 of apparatus 100) for further processing.

In embodiments, the example routine that begins at block 804 may include checking the brain asymmetry results, and then moving to readings of heart rate and respiration rate. Such order of actions of is described for illustration purposes only. Different order of actions may be implemented. For example, heart rate, respiration rate, and brain activity results may be checked in different order, or in parallel.

At block 806, the brain activity data provided by the EEG sensor may be analyzed. The analysis of the brain activity readings may be provided as follows:

1. Initialize stress value=0.0 for the EEG sensor, wherein the stress value is the initial value for the asymmetry index.

2. Run a loop at a sampling rate (e.g., 10 second loop at 200 Hz) to pull data from pins 0 and 1 of the ADC with which the EEG sensor is connected, and storing the pulled data in respective data arrays, newarray0 and newarray1.
3. Perform FFT, and get maximum values between 3 Hz and 17 Hz for newarray0 and newarray1 for alpha waves. As noted above, FFT may be performed on both arrays, discarding the results before 3 Hz and after 17 Hz to remain in the alpha and lower beta range. The peak amplitude in this range may be identified. The ratio of the peak amplitudes from both arrays is defined as the asymmetry index.
4. Determine the percentage increase in the current index from the baseline index. Baseline index may be found by taking the ratio of peak amplitudes of FFTs in relaxed state. Asymmetry index may be continuously measured and compared with the baseline index. As soon as the current asymmetry index goes above a particular value of the baseline index (e.g., the 1.4 times the baseline index), it may crosses the set threshold and record an initial stress event. Then, the thresholds related to the heart rate sensor and microphone may be verified to establish the stress event. The threshold value of the baseline index (e.g., 1.4 times the baseline index) may be determined empirically.

At decision block 808, a determination may be made on whether the brain activity (stress value) is above the threshold. For example, the stress value may be checked against the threshold value. In other words, if a brain activity is determined to be above a threshold, it may be assumed that a stress event is taking place. The threshold value (e.g., 4.5) may be determined empirically, for example, by testing brain activity of a number of individuals.

If the brain activity is above the threshold, a stress event may be recorded at block 810 and the process 800 may move to decision block 812. Otherwise, the process 800 may return to 804.

At decision block 812, a determination may be made on whether the heart rate values exceeded a threshold. For example, it may be checked whether optical heart rate value is more than 100 per minutes. If the heart rate exceeded the threshold, the process 800 may move to decision block 814. Otherwise, the process 800 may return to 804.

At decision block 814, a determination may be made on whether the respiration rate exceeded a threshold. For example, it may be checked whether the respiration rate exceeds 30 breaths per minute. As noted above, the threshold values for heart rate and respiration rate may be determined empirically. Otherwise, the process 800 may return to 804.

If the respiration rate exceeds the threshold, at block 816 a stress event recorded at 810 may be confirmed. A notification about the stress event may be generated and sent to an external device (e.g., 170) to inform the user that the stress event is detected. Corresponding recommendations regarding alleviation of the stress effect may also be provided. Then, the process 800 may return to 804.

The following paragraphs describe examples of various embodiments.

Example 1 may be a wearable apparatus for detecting a stress event, comprising: at least one first sensor disposed on the wearable apparatus to generate a first sensor signal indicative of a brain activity of a user; at least one second sensor disposed on the wearable apparatus to generate a second sensor signal indicative of a heart rate of the user; at least one third sensor disposed on the wearable apparatus to generate a third sensor signal indicative of a respiration rate of the user; and a controller coupled with the at least first, second, and third sensors, to detect a stress event for the user, based at least in part on the first, second, and third sensor signals.

Example 2 may include the wearable apparatus of Example 1, wherein the wearable apparatus comprises a head-fitting device to be mounted at least partly around the user's head, wherein the at least one first sensor is disposed on the head-fitting device to provide direct contact with or proximity to a user's head, in response to application of the head-fitting device to the user's head, wherein the at least one second sensor is disposed on the head-fitting device to provide direct contact with the user's head, in response to application of the head-fitting device to the user's head, and wherein the at least one third sensor is disposed on the head-fitting device to provide direct contact with or proximity to the user's head, in response to application of the head-fitting device to the user's head.

Example 3 may include the wearable apparatus of Example 1, wherein the at least one first sensor comprises first and second capacitive electrodes, to sense electroencephalogram (EEG) indicative of the brain activity of the user.

Example 4 may include the wearable apparatus of Example 1, wherein the at least one second sensor comprises an optical hear rate sensor, to sense a photoplethysmogram (PPG) indicative of the heart rate of the user.

Example 5 may include the wearable apparatus of Example 1, wherein the at least one third sensor comprises one of: a piezoelectric sensor, to sense vibrations in the user's head produced by user's respiration; or a digital or analog microphone, to sense audio signals indicative of the user's respiration rate.

Example 6 may include the wearable apparatus of Example 2, wherein the head-fitting device comprises eyeglasses having a frame with nose pads, wherein the at least one first, second, and third sensors are mounted or removably attached to the frame or nose pads, to be placed adjacent to a nose, temple, ears, or forehead of the user's head, in response to application of the eyeglasses to the user's head.

Example 7 may include the wearable apparatus of Example 6, wherein the at least one first sensor is mounted or removably attached to a side of the frame.

Example 8 may include the wearable apparatus of Example 6, wherein the at least one second sensor is mounted or removably attached to a side of the frame or to one of the nose pads.

Example 9 may include the wearable apparatus of Example 6, wherein the at least one third sensor is mounted or removably attached to the frame or to another one of the nose pads, to provide the direct contact with the user's head.

Example 10 may include the wearable apparatus of Example 1, wherein the controller to detect a stress event includes to: analyze the first, second, and third sensor signals, to identify changes in the brain activity, heart rate, and respiration rate respectively; determine whether the changes in the brain activity, heart rate, and respiration rate exceed respective first, second, and third thresholds within a same time period; and identify the stress event based at least in part on a result of the determination.

Example 11 may include the wearable apparatus of Example 2, wherein the head-fitting device comprises one of: a helmet, a headset, a patch, or other type of headwear.

Example 12 may be a method for detecting a stress event, comprising: receiving, by a controller coupled with a wearable apparatus, a first sensor signal indicative of a brain activity of a user from at least one sensor of the wearable apparatus, a second sensor signal indicative of a heart rate of the user from at least one second sensor of the wearable apparatus, and a third sensor signal indicative of a respiration rate of the user from at least one third sensor of the wearable apparatus; and detecting, by the controller, a stress event for the user, based at least in part on the first, second, and third sensor signals.

Example 13 may include the method of Example 12, wherein detecting a stress event includes analyzing, by the controller, the first, second, and third sensor signals, to identify changes in the brain activity, heart rate, and respiration rate respectively.

Example 14 may include the method of Example 13, wherein detecting a stress event further includes: determining, by the controller, whether the changes in the brain activity, heart rate, and respiration rate exceed respective first, second, and third thresholds within a same period of time; and identifying, by the controller, the stress event based at least in part on a result of the determining.

Example 15 may include the method of Example 14, further comprising: initializing, by the controller, the first, second, and third sensors, including calibrating at least the first sensor, to provide baseline brain asymmetry parameters associated with the brain activity.

Example 16 may include the method of Example 15, wherein the baseline asymmetry parameters include an alpha asymmetry index associated with an alpha brain wave and a beta asymmetry index associated with a beta brain wave.

Example 17 may be one or more non-transitory controller-readable media having instructions for detecting a stress event stored thereon that, in response to execution on a controller coupled with a wearable apparatus, cause the controller to: receive a first sensor signal indicative of a brain activity of a user from at least one sensor of the wearable apparatus, a second sensor signal indicative of a heart rate of the user from at least one second sensor of the wearable apparatus, and a third sensor signal indicative of a respiration rate of the user from at least one third sensor of the wearable apparatus; and detect a stress event for the user, based at least in part on the first, second, and third sensor signals.

Example 18 may include the non-transitory controller-readable media of Example 17, wherein the instructions that cause the controller to detect a stress event further cause the controller to: analyze the first, second, and third sensor signals, to identify changes in the brain activity, heart rate, and respiration rate respectively; determine whether the changes in the brain activity, heart rate, and respiration rate exceed respective first, second, and third thresholds within a same time period; and identify the stress event based at least in part on a result of the determination.

Example 19 may include the non-transitory controller-readable media of Example 18, wherein the instructions that cause the controller to determine whether the changes in the brain activity, heart rate, and respiration rate exceed respective first, second, and third thresholds further cause the controller to first determine whether the brain activity exceeded the first threshold, and determine whether the changes in the heart rate and respiration rate exceed respective second and third thresholds based on a result of the first determination.

Example 20 may include the non-transitory controller-readable media of Example 19, wherein the instructions further cause the controller to provide a notification of the stress event to an external device.

Example 21 may be a wearable apparatus for detecting a stress event, comprising: means for receiving a first sensor signal indicative of a brain activity of a user from at least one sensor of the wearable apparatus, a second sensor signal indicative of a heart rate of the user from at least one second sensor of the wearable apparatus, and a third sensor signal indicative of a respiration rate of the user from at least one third sensor of the wearable apparatus; and means for detecting a stress event for the user, based at least in part on the first, second, and third sensor signals.

Example 22 may include the wearable apparatus of Example 21, wherein means for detecting a stress event includes means for analyzing the first, second, and third sensor signals, to identify changes in the brain activity, heart rate, and respiration rate respectively.

Example 23 may include the wearable apparatus of Example 22, wherein means for detecting a stress event further includes: means for determining whether the changes in the brain activity, heart rate, and respiration rate exceed respective first, second, and third thresholds within a same period of time; and means for identifying the stress event based at least in part on a result of the determining.

Example 24 may include the wearable apparatus of Example 23, further comprising: means for initializing the first, second, and third sensors, including calibrating at least the first sensor, to provide baseline brain asymmetry parameters associated with the brain activity.

Example 25 may include the wearable apparatus of Example 24, wherein the baseline asymmetry parameters include an alpha asymmetry index associated with an alpha brain wave and a beta asymmetry index associated with a beta brain wave.

Various operations are described as multiple discrete operations in turn, in a manner that is most helpful in understanding the claimed subject matter. However, the order of description should not be construed as to imply that these operations are necessarily order dependent. Embodiments of the present disclosure may be implemented into a system using any suitable hardware and/or software to configure as desired.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims and the equivalents thereof.

What is claimed is:

1. A wearable apparatus, comprising:
eyeglasses having a frame comprising a front portion with first and second nose pads, and first and second sides coupled with the front portion;
at least one first sensor that comprises first and second capacitive electrodes, to sense electroencephalogram (EEG) indicative of a brain activity of a user, and generate a first sensor signal indicative of the brain activity of the user, wherein the first and second capacitive electrodes are disposed on the first and second sides of the frame respectively;
at least one second sensor that comprises an optical heart rate sensor, to sense a photoplethysmogram (PPG) indicative of a heart rate of the user, and generate a second sensor signal indicative of the heart rate of the user, wherein the optical heart rate sensor is disposed on the frame or on one of the first or second nose pads, to provide direct contact with a user's head;

at least one third sensor that comprises one of: a piezoelectric sensor, to sense vibrations in the user's head produced by user's respiration; or a digital or analog microphone, to sense audio signals indicative of a user's respiration rate, and generate a third sensor signal indicative of the respiration rate of the user, wherein the third sensor is disposed on the frame or on another one of the first or second nose pads; and a controller disposed on the frame and coupled with the at least first, second, and third sensors, wherein the controller is to:

receive and analyze the first, second, and third sensor signals, to identify changes in the brain activity, heart rate, and respiration rate respectively;

determine whether the changes in the brain activity, heart rate, and respiration rate exceed respective first, second, and third thresholds within a same time period; and generate an indication of a stress event based at least in part on a result of the determination.

2. The wearable apparatus of claim 1, wherein the at least one first sensor is disposed on the wearable apparatus to provide direct contact with or proximity to a user's head, in response to application of the wearable apparatus to the user's head, wherein the at least one second sensor is disposed on the wearable apparatus to provide direct contact with the user's head, in response to application of the wearable apparatus to the user's head, and wherein the at least one third sensor is disposed on the wearable apparatus to provide direct contact with or proximity to the user's head, in response to application of the wearable apparatus to the user's head.

3. The wearable apparatus of claim 1, wherein the at least one first, second, and third sensors are mounted or removably attached to the eyeglasses, to be placed adjacent to a nose, temple, ears, or forehead of the user's head, in response to application of the eyeglasses to the user's head.

4. A method, comprising:

receiving, by a controller coupled with a wearable apparatus comprising eyeglasses having a frame including a front portion with first and second nose pads, and first and second sides coupled with the front portion, the controller disposed on the frame:

a first sensor signal indicative of a brain activity of a user from at least one sensor of the wearable apparatus, the at least one first sensor comprising first and second capacitive electrodes, to sense electroencephalogram (EEG) indicative of the brain activity of the user, and generate the first sensor signal indicative of the brain activity of the user, wherein the first and second capacitive electrodes are disposed on the first and second sides of the frame respectively;

a second sensor signal indicative of a heart rate of the user from at least one second sensor of the wearable apparatus, the at least one second sensor comprising an optical heart rate sensor, to sense a photoplethysmogram (PPG) indicative of a heart rate of the user, and generate the second sensor signal indicative of the heart rate of the user, wherein the optical heart rate sensor is disposed on the frame or on one of the first or second nose pads, to provide direct contact with a user's head; and a third sensor signal indicative of a respiration rate of the user from at least one third sensor of the wearable apparatus, the at least one third sensor comprising one of: a piezoelectric sensor, to sense vibrations in the user's head produced by user's respiration; or a digital or analog microphone, to sense audio signals indicative of a user's respiration rate, and generate the third sensor signal indicative of the respiration rate of the user, wherein the third sensor is disposed on the frame or on another one of the first or second nose pads;

analyzing, by the controller, the first, second, and third sensor signals, to identify changes in the brain activity, heart rate, and respiration rate respectively;

determining, by the controller, whether the changes in the brain activity, heart rate, and respiration rate exceed respective first, second, and third thresholds within a same time period; and generating, by the controller, an indication of a stress event for the user, based at least in part on a result of the determining.

5. The method of claim 4, further comprising: initializing, by the controller, the first, second, and third sensors, including calibrating at least the first sensor, to provide baseline brain asymmetry parameters associated with the brain activity.

6. The method of claim 5, wherein the baseline asymmetry parameters include an alpha asymmetry index associated with an alpha brain wave and a beta asymmetry index associated with a beta brain wave.

7. One or more non-transitory controller-readable media having instructions stored thereon that, in response to execution on a controller, coupled with a wearable apparatus that comprises eyeglasses having a frame that includes a front portion with first and second nose pads, and first and second sides coupled with the front portion, wherein the controller is disposed on the frame, cause the controller to:

receive a first sensor signal indicative of a brain activity of a user from at least one sensor of the wearable apparatus, wherein the at least one first sensor comprises first and second capacitive electrodes, to sense electroencephalogram (EEG) indicative of the brain activity of the user, and generate the first sensor signal indicative of the brain activity of the user, wherein the first and second capacitive electrodes are disposed on the first and second sides of the frame respectively;

receive a second sensor signal indicative of a heart rate of the user from at least one second sensor of the wearable apparatus, wherein the at least one second sensor comprises an optical heart rate sensor, to sense a photoplethysmogram (PPG) indicative of a heart rate of the user, and generate the second sensor signal indicative of the heart rate of the user, wherein the optical heart rate sensor is disposed on the frame or on one of the first or second nose pads, to provide direct contact with a user's head;

receive a third sensor signal indicative of a respiration rate of the user from at least one third sensor of the wearable apparatus, wherein the at least one third sensor comprises one of: a piezoelectric sensor, to sense vibrations in the user's head produced by user's respiration; or a digital or analog microphone, to sense audio signals indicative of a user's respiration rate, and generate the third sensor signal indicative of the respiration rate of the user, wherein the third sensor is disposed on the frame or on another one of the first or second nose pads;

analyze the first, second, and third sensor signals, to identify changes in the brain activity, heart rate, and respiration rate respectively;

determine whether the changes in the brain activity, heart rate, and respiration rate exceed respective first, second, and third thresholds within a same time period; and generate an indication of detect a stress event for the user, based at least in part on a result of the determination.

8. The non-transitory controller-readable media of claim 7, wherein the instructions that cause the controller to determine whether the changes in the brain activity, heart rate, and respiration rate exceed respective first, second, and third thresholds further cause the controller to first determine whether the brain activity exceeded the first threshold, and second determine whether the changes in the heart rate and respiration rate exceed respective second and third thresholds based on a result of the first determination.

9. The non-transitory controller-readable media of claim 8, wherein the instructions further cause the controller to provide a notification of the stress event to an external device.

* * * * *